(12) United States Patent
Rudrabhatla et al.

(10) Patent No.: US 8,399,255 B2
(45) Date of Patent: Mar. 19, 2013

(54) IN VITRO FLOWERING/SEED SET LEADING TO PARTIAL OR COMPLETE MALE STERILITY IN GRASSES

(75) Inventors: Sairam Venkata Rudrabhatla, Middletown, PA (US); Rebekah Ellen Templin, Mechanicsburg, PA (US); Shobha Devi Potlakayala, Middletown, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/053,464

(22) Filed: Mar. 22, 2011

(65) Prior Publication Data

US 2011/0239322 A1 Sep. 29, 2011

Related U.S. Application Data

(60) Provisional application No. 61/316,514, filed on Mar. 23, 2010.

(51) Int. Cl.
*A01H 4/00* (2006.01)
(52) U.S. Cl. ...................................................... 435/426
(58) Field of Classification Search .................. None
See application file for complete search history.

(56) References Cited

U.S. PATENT DOCUMENTS

| | | | |
|---|---|---|---|
| 7,547,548 B2 * | 6/2009 | Rudrabhatla et al. | ......... 435/426 |
| 2004/0199936 A1 | 10/2004 | Gaue et al. | |
| 2004/0237133 A1 | 11/2004 | Goldman et al. | |
| 2005/0268357 A1 | 12/2005 | Rudrabhatla et al. | |
| 2006/0005273 A1 | 1/2006 | Rudrabhatla et al. | |
| 2009/0055968 A1 | 2/2009 | Rudrabhatla et al. | |
| 2009/0307793 A1 | 12/2009 | Goldman et al. | |

OTHER PUBLICATIONS

Altpeter et al. Efficient Plant regeneration from mature seed derived embryogenic callus of turf-type bahiagrass (*Paspalum notatum* flugge). International Turfgrass society. Research Journal vol. 10, 2005.*

Havey, Michael J., "Chapter 23—The Use of Cytoplasmic Male Sterility for Hybrid Seed Production", University of Wisconsin, Madison, Wisconsin, Molecular Biology and Biotechnology of Plant Organelles 623-634, Springer 2004 (12 pages).

* cited by examiner

*Primary Examiner* — Annette Para
(74) *Attorney, Agent, or Firm* — McKee, Voorhees & Sease, P.L.C.

(57) ABSTRACT

The present invention relates to a method of manipulating plant development that allows for partial or complete male sterility in grasses.

11 Claims, No Drawings

IN VITRO FLOWERING/SEED SET LEADING TO PARTIAL OR COMPLETE MALE STERILITY IN GRASSES

CROSS-REFERENCE TO RELATED APPLICATIONS

This application claims priority under 35 U.S.C. §119 to provisional application Ser. No. 61/316,514 filed Mar. 23, 2010, herein incorporated by reference in its entirety.

FIELD OF THE INVENTION

This invention relates to a new method for inducing male sterility in grasses through the application of in vitro flowering techniques and plant hormones.

BACKGROUND OF THE INVENTION

Heterosis in crop plants can have a marked effect on yield improvement. In general, hybrids exhibit increased yields in comparison with non-hybrid varieties and usually give greater return unit for growth factors such as water and fertilizer. Hybrids often offer superior stress tolerance, uniformity in product and maturity and also afford a simple breeding opportunity to combine characteristics or traits that may be difficult to combine in other ways. Hybrid vigor in plants is generally of sufficient magnitude to warrant commercial exploitation. Commercial hybrids are used extensively in many crops including corn, sorghum, sugar beet, sunflower and canola. Despite the many advantages of hybrid vigor, wheat, barley and rice are still grown mainly as inbreds, primarily due to the lack of economical hybrid seed production methods.

A precondition for the production of hybrid varieties is the directed pollination of a mother line using a selected father line as the pollen donor. In order to produce a sufficient number of seeds, the latter step has to be performed on large-scale and under outdoor conditions. By cultivating a pollenless, i.e. male sterile, mother line and a fertile (pollen-bearing) father line in direct proximity, such a directed pollination is achieved, thereby creating a large number of hybrid seeds that can be directly traced back to the crossing combination of the two parent lines. A precondition particularly for this is the existence of a complete, i.e. if possible, 100% male sterile mother line which cannot pollinate itself.

For this reason various methods were developed in the past, in particular mechanical, chemical and genetic methods for the induction of male sterility of plants. Mechanical methods, such as the removal of the anthers, are only suitable for plant species having large and/or spatially separated sexual organs, such as is the case in corn (*Zea mays* L.). For the chemical emasculation of plants, substances called gametocides were developed, which have a lethal effect on pollen after application. In this way, hybrid varieties of strict self-pollinators such as wheat and barley could be produced for the first time.

Genetic mechanisms that induce male sterility of plants have been previously described. For instance, male sterile plants basically occur in the mostly aneuploid progeny of wide, i.e. inter-specific or intergeneric crossings. This is partly due to irregularities in the meiosis of the progeny affecting both male and female gametes to the same extent. Additional, systems that are based on single gene defects and only influence the male gametes and pollen have been discovered and further refined. Such systems can be traced back on the one hand to mutations in the nuclear genome (nuclear male sterility, NMS) and on the other hand to gene alterations in the plastom or cytoplasm (cytoplasmic male sterility, CMS).

In most higher plants, cytoplasmic male sterility (CMS) is inherited strictly maternally. CMS is based in principle on the incompatibility of the nucleus and the cytoplasm. With the help of a corresponding father line, not able to overcome the sterility of the maternal cytoplasm (so-called "maintainer"), a homozygous sterile CMS plant may theoretically be produced after repeated back-crossing with the maintainer plant. A complete CMS system, for the production of hybrid seeds of grasses whose vegetative mass is used, thus consists of the following components: (1) the CMS line which bears a sterility-inducing cytoplasm (S), also called sterile mother line; (2) the maintainer line, which bears a normal fertile cytoplasm (N) and which is very similar to the CMS line in other respects; (3) the pollinator line or father line, which has normally fertility and is suitable for combination with the CMS mother line.

A fundamental technical problem for the production of hybrid varieties is the stability of male sterility in the CMS line. This particularly affects the 100% transfer of male sterility to the next generation after crossing and the provision of an environmentally independent phenotype in the form of male sterile plants. Only under these conditions can agronomically optimized and complete male sterile mother plants be generated, which permit heterosis in the form of hybrid varieties to be exploited to its full extent and to realize an additional yield potential.

The *Lolium* species perennial ryegrass (*Lolium perenne* L.), annual ryegrass (*Lolium multiflorum* L.) and hybrid ryegrass (*Lolium hybridum* L.) are the most important grass species in European food grass culture. For food grasses the specific exploitation of heterosis effects is thought to be a real possibility for substantially increasing yields and for improving further quantitative characteristics such as stress tolerances against biotic and abiotic factors. As the aforementioned *Lolium* species are cross-pollinators, the opportunity for breeding of synthetics and hybrid varieties presents itself for this purpose.

In order to achieve additional variability as a basis for the selection of new genotypes, the method of polyploidization is used in the breeding of cultured plants. In polyploidization, using mitosis inhibitors such as colchicine during mitosis allows the chromosome set of a cell to be doubled. In the case of *Lolium* species this leads to the generation of tetraploid forms from originally diploid species (2n=2x=14), which have a double chromosome set (2n=4x=28). Because tetraploids possess other characteristics besides diploids, for the economically relevant *Lolium* species *L. perenne*, *L. multiflorum* and *L. hybridum* corresponding tetraploid varieties have been cultivated.

For ryegrass species numerous studies point to heterosis and hybrid growth in all valences (including C. A. Foster, Interpopulational and intervarietal hybridization in *Lolium perenne* breeding, heterosis under noncompetitive conditions, J. Agric. Sci. 1971, 107-130; C. A. Foster, (1973): Interpopulational and intervarietal $F_1$-Hybrids in *Lolium perenne*: performance in field sward conditions, J. Agric. Sci. 1973, 80, 463-477; I. Rod, Beitrag zu den methodischen Fragen der Heterosiszuchtung bei Futtergrasern, Ber. Arbeitstagung Arbeitsgemeinsch. Saatzuchtleiter Gumpenstein 1965, pages 235-252; I. Rod, Remarks on heterosis with grasses, Heterosis in plant breeding, Proc. 7th Congr. Eucarpia Budapest (1967), pages 227-235; A. J. Wright, A theoretical appraisal of relative merits of 50% hybrid and synthetic, J. Agric. Sci. 79, 1972, pages 245-247). In the past, heterosis effects could be detected particularly after single plant crossings, line crossings and variety crossings (Kobabe, see above).

The breeding method most commonly used at present, namely the production of synthetics or varieties on the basis of clones or populations, was developed for grasses by Frandsen in 1940 (N. H. Frandsen, Some breeding experiments with timothy, Imp. Agric. Bur. Joint Publ. 1940, 3, 80-92). As mentioned above, however, this method only allows a partial use of heterosis. A true food grass hybrid variety using a *Lolium* line with cytoplasmic male sterility for the complete utilization of heterosis (C. Bothe, see above; G. Kobabe, see above; V. Lein, see above) is not known so far, because no plants with complete male sterility were available and the known CMS sources are unstable.

The systems found or used for *Lolium* species for the achievement of male sterility differ with respect to their origin and mode of action. Systems with mechanical control for the castration of the plants are ruled out for *Lolium* species due to their morphology. Chemical methods have not yet been developed for *Lolium*, while genetic control mechanisms were described previously. Spontaneously generated sources have been reported by Nitzsche (Cytoplasmatische mannliche Sterilitat bei Weidelgras (*Lolium* ssp.) Z. Pflanzenzucht., Berlin (West) 65, (1971), pages 206-220) for *Lolium multiflorum*, and, for *Lolium perenne*, by Gaue (Moglichkeiten der Hybridzuchtung auf ms-Basis bei *Lolium perenne* L. XIII. Internat. Grasland-Kongreβ, Leipzig 1977, Sektionsvortrag 1-2, pages 491-496; Ergebnisse von Untersuchungen zur Hybridzuchtung bei *Lolium perenne* Tag.-Ber., Akad. Landwirtsch.-Wiss. DDR, Berlin (1981) 191, pages 119-126). After species and genus crossings male sterile forms also developed for *Lolium perenne* (F. Wit, Cytoplasmic male sterility in ryegrasses (*Lolium* ssp.) detected after intergeneric hybridization, Euphytica 1974, 23, 31-38; V. Connoly, Hybrid grasses varieties for the future Farm Food Res. 1978, 9, 6, 131-132; V. Connoly, R. Wright-Turner, Induction of cytoplasmic male-sterility into ryegrass (*Lolium perenne*), Theor. Appl. Genet. 1984, 68, 449-453). None of these genetic systems could however be stabilized genotypically and phenotypically, so that as yet no functional hybrid system is known for the different ryegrass species.

Although the production of hybrid lines with improved agronomic characteristics is intensively studied, methods available so far for the production of male sterile plants do not lead to completely satisfactory results in many cases. Therefore a strong need for a method for the production of completely male sterile and stable plants that do not show the disadvantages of the prior art is clearly indicated.

SUMMARY OF THE INVENTION

The present invention provides a method for inducing partial or complete male sterility in grasses and other similar monocots by an in vitro methodology. This method involves transferring callus formation to regeneration medium containing specific plant hormones. Quite surprisingly, the applicant has found that the generation of in vitro plant flowering in the presence of tissue culture media with specific hormones leads to partial and complete male sterility in grasses.

The process involves the steps of a) sterilizing grass seeds, b) germinating the seeds on basal medium containing an auxin, c) removing the end of the shoot, preferably the first internode, and placing again in basal medium with auxin, d), transferring the resultant callus into regeneration medium containing a cytokine, auxin, and CuSO4, e) after shoots form from the callus, transferring the callus to the final regeneration medium of basal medium, a substituted phenylurea cytokine analog, an auxin, a cytokine, and CuSO4.

More specifically, the process involves germinating sterilized seeds on basal medium containing MS and 4 mg 2,4-D. Transferring the callus to regeneration medium containing MS, 0.5 mg/L BAP, 0.1 mg/L 2,4-D, 38 mg/L CuSO4 and after shoots are formed, transferring the callus to final regeneration medium of MS, 2 mg/L TDZ, 1 mg/L BAP, 38 mg/L CuSO4.

Sterilizing the seeds can be by any of a number of standard protocols including sulfuric acid, bleach, or mercuric chloride.

DETAILED DESCRIPTION OF THE INVENTION

Definitions

In order to provide a clear and consistent understanding of the specification and claims, including the scope to be given to such terms, the following definitions are provided.

We define "in vitro flowering" as direct flower production on a plant derived from a mass of undifferentiated cells (callus). The immediate result of in vitro flowering is the production of flowers that are sterile as in case of monocotyledonous plants. In vitro flowering encompasses precocious flowering where the flowers are produced directly from explants having a reduced life cycle but never produce viable seed. The in vitro flowering of the present invention leading to partial or complete male sterility provides methods of eliciting different developmental fates from cells of an explant by application of a unique novel growth regulator regime. These developmental fates include, but are not limited to: (1) directly producing flower (2) in vitro developed shoots from explants leading to the formation of sterile flowers; (These directed cell fate shifts result from a manipulation of growth regulators in defined concentrations and/or combinations that dictate the cell fate shifts of each explanted tissue).

These directed developmental fates have been identified in response to different growth regulators and, in combination or alone, and as a function of growth regulator concentration, time of application, and choice of explanted tissue and application of copper sulfate. The present invention also provides novel in vitro flowering media, which constitute a unique advance in the field of cell fate determination since different hormonal combinations in combination with a specified explant control different developmental outcomes (e.g. the same meristematic cells will respond differentially to different hormonal combinations). For example, flowers and shoots with a hormone profile (2.0 mg/l TDZ and 1.0 mg/l BAP).

"Untransformed cells" as used herein refers to cells that have not been contacted with a particular DNA fragment or gene of interest, which will be used when applying the method of the invention. Such cells may also be derived from a transgenic plant or plant tissue that had been previously transformed with a different or similar DNA fragment or gene of interest.

"Efficiency of transformation" or "frequency of transformation" as used herein refers to the likelihood that a population of cells/plants will be transformed with a gene of choice. "Efficiency of transformation" or "frequency of transformation" can be measured by the number of transformed cells/plants (or transgenic organisms grown from individual transformed cells) that are recovered from a population of cells.

A "transgenic plant" as used herein contains cells that replicate a gene of interest (referred to herein as a "delivered gene") and pass the gene of interest to each daughter cell in each generation and to the progeny of the next. The gene of interest may be covalently linked either to nuclear DNA and/or plastid DNA. As a result, the delivered gene is integrated in the DNA and passes from one generation to the next. Plastid DNA is maternally inherited during sexual reproduction. The delivered gene(s) include DNA from a wide range of plant, animal, fungal, bacterial, viral, and protists sources, as well as DNA homologous to the recipient plant. The delivered gene can include selectable and/or screenable markers. However, a delivered gene need not be linked to a selectable marker. In this case, transgenic cells can be identified following co-transformation using two separate agrobacterium plasmids. Transgenic plants express at least one additional homologous, foreign or plant-optimized gene. Transgenic plants may be produced using the method of the present invention by combining in vitro flowering with a transformation method, and, and subsequent regeneration of the plant from the transformed cells. Acceptable transformation methods are known in the art and include, but are not limited to, agrobacterium-mediated-transformation, chloroplast transformation, biolistics, electroporation, polyethylene glycol ("PEG") mediated transformation, protoplast mediated DNA uptake, and whisker mediated transformation.

"MS basal medium" is known in the art and was originally described by Murashige and Skoog, Physiology Plantarum 15:473-497 (1962). In the methods and media of the present invention, "MS basal medium" or "MS medium" as used herein includes MS basal medium as described by Murashige and Skoog as well as equivalents of MS basal medium. One skilled in the art would understand that equivalents of MS basal medium include media that is substantially similar in contents and concentrations of salts, chemicals, etc., such that a tissue or plant would develop/grow in the same manner when exposed to MS basal medium.

MS basal medium with $B_5$ vitamins ("$MSB_5$ medium") is known as was originally described by Gamborg, O. L.; Miller, R. A.; Ojima, K., Exp. Cell Res. 50:151-158 (1968). In the methods and media of the present invention, "$MSB_5$" as used herein includes MS basal medium as described by Murashige and skoog and $B_5$ vitamins as described by Gamborg as well as equivalents of $MSB_5$. One skilled in the art would understand that equivalents of $MSB_5$ include media that is substantially similar in contents and concentrations of salts, chemicals, vitamins, etc. such that a tissue or plant would develop/grow in the same manner when exposed to $MSB_5$.

"Plant growth regulators" as used herein, is a synonymous term with "Plant Hormones." "Plant growth regulators" or "plant hormones" as used herein are those hormones that promote root induction, cell division and cell elongation that lead to the formation of shoots, roots, flowers and seed. Plant growth regulators have been commonly classified into five groups: auxins, cytokinins, gibberellins, ethylene and abscisic acid.

"Auxins" include, but are not limited to, naturally occurring and synthetic auxins. Naturally occurring auxin is indole acetic acid ("IAA"), which is synthesized from tryptophan. An exemplary synthetic auxin in dichlorophenoxyacetic acid ("2,4-D"). Other auxins include, but are not limited to, 4-chlorophenoxyacetic acid ("4-CPA"), 4-(2,4-dichlorophenoxy)butyric acid ("2,4-DB"), tris[2-(2,4-dichlorophenoxy)ethyl]phosphite ("2,4-DEP"), 2-(2,4-Dichlorophenoxy) propionic acid ("dichloroprop"), (RS)-2-(2,4,5-trichlorophenoxy)propionic acid ("fenoprop"), naphthaleneacetamide, α-naphthaleneacetic acid ("NAA"), 1-naphthol, naphthoxyacetic acid, potassium naphethenate, (2,4,5-trichlorophenoxy) acetic acid ("2,4,5-T"), indole-3-acetic acid, indole-3-butyric acid ("IBA"), 4-amino-3,5,6-trichloropyridine-2-carboxylic acid ("picloram"), 3,6-dichloro-o-anisic acid ("dicamba"), indole-3-proionic acid ("IPA"), phenyl acetic acid ("PAA"), benzofuran-3-acetic acid ("BFA"), and phenyl butric acid ("PBA"). A primary site of auxin production is the apical shoot meristem and the most studied function of auxin is the promotion of elongation and cell enlargement. Auxins also promote lateral and adventitious root development.

"Cytokinins" are a group of phenylurea derivatives of adenine. Cytokinins promote cytokinesis (division of the cytoplasm to a cell following the division of the nucleus). Cytokinins also retard leaf senescence. The first naturally occurring cytokinin chemically identified was called zeatin. An exemplary synthetic cytokinin is 6-benzylamino purine ("BAP"). Examples of cytokinins include, but are not limited to, 6-γ,γ-Dimethylallylaminopuine ("2iP"), kinetin, zeatin, zeatin riboside, and BAP.

"Substituted phenylurea cytokinin analogs" are cytokinin analogs and have cytokinin-like activity. It is believed that these analogs are not metabolized by plants. "Substituted phenylurea cytokinin analogs" as used herein include, but are not limited to, 1-phenyl-3-(1,2,3-thiadiazol-5-yl)urea ("thidiazuron" or "TDZ"), carbanilide (1,3,-diphenyl urea) ("DPU"), and N-(2-chloro-4-pyridyl)-N'-phenylurea ("CPPU").

Giberrellins are derived from the ent-gibberellane skeleton. Gibberellins are diterpenes synthesized from acetyl CoA via the mevalonic acid pathway. They all have either 19 or 20 carbon units grouped into either four or five ring systems. The gibberellins are named $GA_1 \ldots GA_n$ in order of discovery. Gibberellic acid, which was the first gibberellin to be structurally characterized, is GA3, and is the most commonly used giberrellin. There are currently 136 GAs identified from plants, fungi and bacteria. Giberrellins are generally used to promote flowering, break dormancy of seeds, buds, corms, and bulbs, and cause stem elongation.

"Gene" as used herein includes any informational hereditary unit including regulatory sequences as well as those nucleic acid sequences involved in protein expression within the cells (including both prokaryotic and eukaryotic), including chimeric DNA constructions, plant genes and plant-optimized genes.

"Plant gene" as used herein means a gene encoded by a plant.

Plant-optimized gene" as use herein means a homologous or heterologous gene designed for plant expression.

"Gene of interest" or "delivered gene" may be homologous DNA, heterologous DNA, foreign DNA, genomic DNA or cDNA.

"Stacked genes" of interest are those containing more than one gene(s) that confers value-added traits or phenotypes linked to between either the right and left T-DNA border sequences or covalently linked to the right border sequence. Alternatively, stacked genes refers to a multiple of genes that have been delivered and integrated in the host DNA of the plant cell by more than one recombination event, as in the case of co-transformation. In co-transformation, the T-DNA constructs are in independent Agrobacterium strains.

"Expression" means the transcription and stable accumulation of the mRNA and/or protein within a cell. Expression of genes involves transcription of DNA into RNA, processing of the RNA into mRNAs in eukaryotic systems, translation of mRNA into precursor and mature proteins, followed, in some cases, by post-translational modification. This definition in no way limits expression to a particular system and is meant to include all types including cellular, transient, in vitro, in vivo, and viral expression systems in both prokaryotic and eukaryotic cells.

"Organogenesis" means a process by which shoot and roots are developed sequentially under in vitro conditions from any meristematic tissue.

"Embryogenesis" is a process of differentiation that is characterized by the formation of organized structures that resemble zygotic embryos from which shoots and roots may be produced in vitro.

"Male-sterile plant" as used herein is a plant that is incapable of supporting viable pollen formation. Such male sterility can be the result of breeding selection or the presence of a transgene or can be a result of treatment of copper sulfate or can be due to presence of growth regulators. A "conditionally male-sterile plant" refers to a plant which under normal growing conditions is male fertile and which can become male-sterile under specific conditions. For example the conditions might comprise physical emasculation or application of a specific chemical gametocide. In the context of the current invention the said conditions particularly comprise the exogenous application of a pro-herbicide or other non-phytotoxic substance. In the context of the current invention such a "male-sterile plant" or "conditionally male-sterile plant" remains female fertile and able to produce viable seeds when pollinated with functional or viable pollen.

The present invention provides a method to produce male sterile grasses for development of hybrid cultivars and the like that are useful for multiplication of seed with value-added traits generated through conventional breeding and/or for rapid and efficient production of transgenic seeds under conditions of complete pollen containment.

In additional embodiments of the present invention, any of the methods herein can be used for the production of stable F1 hybrids of completely male sterile plants of the graminoids, which are monocotyledonous, usually herbaceous plants with narrow leaves growing from the base. They include the "true grasses", of the Poaceae (or Gramineae) family, (including *Lolium* etc) as well as the sedges (Cyperaceae) and the rushes (Juncaceae). The true grasses include cereals, bamboo and the grasses of lawns (turf) and grassland. Sedges include many wild marsh and grassland plants, and some cultivated ones such as water chestnut (*Eleocharis dulcis*) and papyrus sedge (*Cyperus papyrus*).

The methods of the invention may be used to producing a completely male sterile grass plant and back-crossing the male sterile plant thus obtained with one or more plants, lines or varieties, which have normal fertile cytoplasm and which maintain the sterility of the male sterile plants (maintainer plants). In some aspects, the male sterile plants are identified by at least one test method directed to pollen vitality or a molecular biological method. In additional aspects, plants of the corresponding species are used as maintainer plants, which lead to a 100% pollen-sterile progeny after crossing with the male sterile line. In some aspects, a multiple back-crossing with maintainer plants is performed.

Furthermore, the sterility-inducing germplasm of the male sterile plant produced by any of the methods can be brought to a preferably tetraploid valence by polyploidization. This can be achieved, for example, using a colchicine treatment. In further aspects, the method can be used to produce grass plants with complete male sterility. Accordingly, in some embodiments of the invention, grass plants with complete male sterility are provided.

Also, some embodiments relate to, for example, methods for the production of hybrids with pollinator plants having normal male fertility, using the completely male sterile plants according to any of the methods known to those of skill in the art. Additional embodiments relate to, for example, hybrid seeds produced by any of the same.

In another essential aspect of the present invention, plants with complete male sterility are provided, which can be produced according to the method described herein.

A further subject of the invention is a method for the production of stable F1 hybrids of completely male sterile plants of the corresponding species, comprising the following steps: a) producing completely male sterile plants of the corresponding species according to the method described herein, and b) back-crossing the male sterile plants obtained from step a) with plants of the same species, which carry a normal fertile cytoplasm and which maintain the sterility of the male sterile plants (maintainer plants).

In natural grass populations, a differentiated proportion of maintainer plants are present, which is determined by corresponding test crossings with investigation of the F1 generation on sterility.

A stable male sterile line is preferably obtained by repeated back-crossing with maintainer lines.

Generally the male sterile plants are obtained through culture techniques according to the following. The process involves the steps of a) sterilizing grass seeds, b) germinating the seeds on basal medium containing an auxin, c) removing the end of the shoot, preferably the first internode, and placing again in basal medium with auxin, d), transferring the resultant callus into regeneration medium containing a cytokine, auxin, and CuSO4, e) after shoots form from the callus, transferring the callus to the final regeneration medium of basal medium, a substituted phenylurea cytokinin analog, an auxin, a cytokine, and CuSO4.

More specifically, the process involves germinating sterilized seeds on basal medium containing MS and 4 mg, 2,4-D. Transferring the callus to regeneration medium containing MS, 0.5 mg/L BAP, 0.1 mg/L 2,4-D, 38 mg/L CuSO4 and after shoots are formed, transferring the callus to final regeneration medium of MS, 2 mg/L TDZ, 1 mg/L BAP, 38 mg/L CuSO4.

In a preferred embodiment, seeds are washed in running tap water with a drop of soap for 5 mins and sterilized with 95% ethyl alcohol for 2 min followed by a 15 minute treatment with 10% bleach and washed three times for 5 min intervals with sterile distilled water. Ten seeds are germinated in each petriplate with MS medium with 4 mg 2,4-D. After germination on MS 2,4-D, for a period of time, such as 3-7 days in the dark at 24±2° C. The flowering medium preferably comprises a substituted phenylurea cytokinin analog, such as TDZ and a cytokinin such as BAP.

Cultures are incubated at 24±2° C. under a 16/8-hour dark photoperiod provided by cool-white fluorescent lights at a quantum flux density of 30 µmol s$^{-1}$ m$^{-2}$. Following a passage of time, typically within 2 weeks, callus induction occurs, having taken the first internode of the germinated seed (on MS 4 mg/L 2,4-D medium). After about two weeks, the callus is transferred to regeneration medium, to allow for shoot induction (MS, 0.5 mg/L BAP, 0.1 mg/L 2,4-D, 38 mg/L CuSO4). During this time (shoot regeneration), cultures are incubated with necessary dark photoperiodic conditions to promote growth and to mimic natural growing conditions. Additionally, over time it may be necessary to subculture the explants with fresh MS, BAP, 2,4-D, CuSO4.

After shoots have appeared and grown, the callus is once again transferred, to flowering medium of MS, 2 mg/L TDZ, 1 mg/L BAP, 38 mg/L CuSO4.

This method as well as the other methods of the present invention described herein below may also be practiced in other tissue culture systems in addition to petri dishes. One skilled in the art would appreciate that other acceptable plant tissue culture systems exist. For example, the use of Magenta™ vessels, Magenta™ Membrane Raft, or Osmotek's Life Raft may be successfully employed.

Flowering Medium

Another embodiment of the invention provides a medium comprising MS medium and at least one substituted phenylurea cytokinin analog which is used to induce male sterility. A callus from which shoots arise when placed on a flowering medium produces flower buds. An exemplary substituted phenylurea cytokinin analog is (N-phenyl-N'-1,2,3-thidiazol-5-ylurea) (also known as "Thidiazuron" or "TDZ"). TDZ is a bio-regulator of morphogenesis in tissue culture of many plant species. A substituted phenylurea cytokinin analog or mixtures thereof may be present in the flowering medium at a concentration of about 0.1 mg/L to about 5.0 mg/L (and any concentration within that range), alone or in combination with a cytokinin and/or auxin as described below. A preferred concentration of a substituted phenylurea cytokinin analog is about 1.0 mg/L to about 4.0 mg/L. A more preferred concentration is about 1.5 mg/L to about 3.0 mg/L. An especially preferred concentration of a substituted phenylurea cytokinin analog is about 1.5 mg/L to about 2.5 mg/L. A most preferred concentration of a substituted phenylurea cytokinin analog is about 2.0 mg/L.

In preferred embodiments, a substituted phenylurea cytokinin analog is TDZ and is present in a flowering medium at a concentration of about 0.1 mg/L to about 5.0 mg/L (and any concentration within that range), alone or in combination with other cytokinins and/or auxins as described below. A preferred concentration of TDZ is about 1.0 mg/L to about 4.0 mg/L. A more preferred concentration of TDZ is about 1.5 mg/L to about 3.0 mg/L. An especially preferred concentration of TDZ is about 1.5 mg/L to about 2.5 mg/L. A most preferred concentration of TDZ is about 2.0 mg/L.

A flowering medium may also contain plant hormones, known as cytokinins. Exemplary cytokinins include but are not limited to benzyl amino purine ("BAP"), zeatin, and kinetin, as well as others discussed above in the definitions and as known by one skilled in the art. Cytokinins play an important physiological effect on plant growth and morphology as they promote shoot formation and lateral bud expansion and delay leaf senescence through their functions in promoting cell division and cell differentiation.

Cytokinin(s) or mixtures thereof may be present in a flowering medium at a concentration of about 0.5 mg/L to about 4.0 mg/L (and any concentration within that range). A preferred concentration is about 0.5 mg/L to about 3.0 mg/L. A more preferred concentration is about 0.75 mg/L to about 2.5 mg/L. An especially preferred concentration of cytokinin is about 0.75 mg/L to about 1.5 mg/L. A most preferred concentration of BAP is about 1 mg/L.

In preferred embodiments, a cytokinin is BAP and may be present in a flowering medium at a concentration from about 0.5 mg/L to about 4.0 mg/L (and any concentration within that range). A preferred concentration of BAP is about 0.5 mg/L to about 3.0 mg/L. A more preferred concentration of BAP is about 0.75 mg/L to about 2.5 mg/L. An especially preferred concentration of BAP is about 0.75 mg/L to about 1.5 mg/L.

When TDZ (2.0 mg/L) is combined with BAP (1.0 mg/L), cell fate is altered and flowers are produced directly on a shoot explant. While this hormone combination is preferred, other combinations and concentrations of cytokinins also produce flowers directly on a shoot. For example, TDZ (1.0-2.0 mg/L) without BAP also produces flowers on shoots developed from callus. It appears that TDZ concentration in an in vitro flowering medium is an important parameter in reducing or increasing flower bud formation.

A flowering medium of the present invention may also contain auxins in addition to, or instead of, cytokinins Exemplary auxins include, but are not limited to, naphthalene acetic acid ("NAA"), indole acetic acid ("IAA"), 2,4-dicholoropehonoxyacetic acid ("2,4-D"), indole-3-proionic acid ("IPA"), indole-3-butyric acid ("IBA"), phenyl acetic acid ("PAA"), benzofuran-3-acetic acid ("BFA"), phenyl butric acid ("PBA"), dicamba, picloran and others discussed above in the definitions and known by one skilled in the art. Auxins also play an important role on plant growth and morphology in that they promote apical dominance, lateral and adventitious root formation, stem elongation and leaf elongation by promoting cell elongation.

A flowering medium is prepared by supplementing a MS medium with a desired substituted phenylurea cytokinin analog, and/or a cytokinin, and/or auxin, or mixtures thereof as described above. The medium is augmented with 3% sucrose. If the medium is to be used on a solid state culture, e.g. petri dish, the medium is solidified with 0.5 to 0.75% agar (Phytochech Labs). The pH of the medium is adjusted to 5.8 with 0.1 M NaOH or 0.1 M HCl before autoclaving at 1.4 kg cm$^{-2}$ for 20 mins at 121° C. After sterilization 20 ml of this medium is dispensed in to each sterile petriplate (100×15 mm).

6 different varieties of Ryegrass plants were prepared according to the aforementioned practices and shown to have 50% of spikes with sterility and 50% with seed set.

What is claimed is:

1. A method for producing ryegrass plants, comprising:
   a) germinating at least one ryegrass seed on an auxin-containing MS medium to produce a shoot, removing the end of the shoot comprising the first internode, and transferring the removed end to an auxin-containing MS medium to produce callus from the shoot end;
   b) transferring the callus to a shoot-induction medium comprising an auxin, a cytokine, and CuSO4 until shoots are formed;
   c) followed by transferring the callus comprising the shoots to a flowering medium comprising an auxin, CuSO4 and at least one substituted phenylurea cytokinin analog; and
   d) allowing the shoots on the callus to develop at least one flower bud, thus producing a ryegrass plant which is male sterile or partially male sterile.

2. The method of claim 1 wherein the at least one substituted phenylurea cytokinin analog comprises thidiazuron.

3. The method of claim 2 wherein thidiazuron is present at a concentration of 1.5 mg/L to 2.5 mg/L.

4. The method of claim 3 wherein thidiaruzon is present at a concentration of 2 mg/L.

5. The method of claim 2 wherein the flowering medium further comprises at least one cytokinin.

6. The method of claim 5 wherein the cytokinin is BAP.

7. The method of claim 6 wherein the BAP is present at a concentration from 0.75 mg/L to 1.5 mg/L.

8. The method of claim 7 wherein BAP is present at a concentration of 1 mg/L.

9. The method of claim 1 wherein the flowering medium comprises thidiaruzon and BAP and wherein the concentration of thidiaruzon in the flowering medium is 2.0 mg/L and the concentration of BAP in the flowering medium is 1.0 mg/L.

10. The method of claim 1 wherein the ryegrass seed is sterilized prior to germination, and wherein said shoot induction medium comprises BAP, 2,4-D, and CuSO4.

11. The method of claim 1 wherein said flowering medium comprises thidiaruzon, BAP, and CuSO4.

* * * * *

UNITED STATES PATENT AND TRADEMARK OFFICE
CERTIFICATE OF CORRECTION

PATENT NO. : 8,399,255 B2  
APPLICATION NO. : 13/053464  
DATED : March 19, 2013  
INVENTOR(S) : Sairam Rudrabhatla et al.

Page 1 of 1

It is certified that error appears in the above-identified patent and that said Letters Patent is hereby corrected as shown below:

In the Claims

Col. 10, Claim 4, Line 47:  
DELETE after wherein "thidiaruzon"  
ADD after wherein --thidiazuron--

Col 10, Claim 9, Line 57:  
DELETE after comprises "thidiaruzon"  
ADD after comprises --thidiazuron--

Col. 10, Claim 9, Line 58:  
DELETE after of "thidiaruzon"  
ADD after of --thidiazuron--

Col. 10, Claim 11, Line 65:  
DELETE after comprises "thidiaruzon"  
ADD after composes --thidiazuron--

Signed and Sealed this  
Twenty-first Day of May, 2013

Teresa Stanek Rea  
*Acting Director of the United States Patent and Trademark Office*